United States Patent [19]

Schneider et al.

[11] Patent Number: 5,045,538

[45] Date of Patent: Sep. 3, 1991

[54] INHIBITION OF WASTING AND PROTEIN DEGRADATION OF MAMMALIAN MUSCLE BY TETRACYCLINES

[75] Inventors: Bruce Schneider, Great Neck; Robert A. Greenwald, Melville; Jonathan Maimon, Rego Park; Kenneth Gorray, Fresh Meadows; Lorne M. Golub, Smithtown; Thomas F. McNamara, Port Jefferson; Nangavarum S. Ramamurthy, Smithtown, all of N.Y.

[73] Assignee: The Research Foundation of State University of New York, Albany, N.Y.

[21] Appl. No.: 545,395

[22] Filed: Jun. 28, 1990

[51] Int. Cl.$^5$ ............................................. A61K 31/65
[52] U.S. Cl. ...................................................... 514/152
[58] Field of Search ......................................... 514/152

[56] References Cited

U.S. PATENT DOCUMENTS

| | | | |
|---|---|---|---|
| 4,666,897 | 5/1987 | Golub et al. | 514/152 |
| 4,704,383 | 11/1987 | McNamara et al. | 514/152 |
| 4,925,833 | 5/1990 | McNamara et al. | 514/152 |
| 4,935,411 | 6/1990 | McNamara et al. | 514/152 |
| 4,935,412 | 6/1990 | McNamara et al. | 514/152 |

OTHER PUBLICATIONS

Gorray et al., in *Metabolism* 39, No. 2, 109–116 (1990).
Golub et al., "Further Evidence That Tetracyclines Inhibit Collagenase Activity in Human Crevicular Fluid and from Other Mammalian Sources", *J. Periodont. Res.* 20, 12–23 (1985).
Greenwald et al., "Direct Detection of Collagenase and Gelatinase in Particular Tissue from Adjuvant Arthritic Rats: Inhibition by Tetracyclines and Potential Amelioration of Bone Destruction", Abstract, *Transactions of the Orthopedic Research Society*, vol. 15, p. 270 (1990).
*The Chemistry of Tetracyclines,* (L. A. Mitscher, ed.) Chapter 6, pp. 165–218 (1978).
Golub et al., "Tetracyclines (TCs Inhibit Mealloproteinase (MPs): *In Vitro* Effects of Arthritic and Diabetic Rats, and New In Vitro Studies", Abstract, Matrix Metalloproteinase Conference, p. 43, Sep. 1989.
Sipos et al., "The Effect of Collagenase Inhibitors on Alveolar Bone Loss Due to Periodontal Disease in Desalivated Rats", Abstract, Matrix Metalloprotenase Conference, p. 43, Sep. 1989.
Breedveld et al., "Suppression of Collagen and Adjuvant Arthritis by a Tetracycline", Abstract, Northeastern Regional Meeting of the Amer. Rheum. Assoc., p. 17, Oct. 1987.
Elewski et al., "*In Vivo* Suppression of Neutrophil Chemotaxis by Systemically and Topically Administered Tetracycline", Journal of the American Academy of Dermatology 8, 807–812 (1983).
Skinner et al., "Tetracycline in the Treatment of Rheumatoid Arthritis—a Double Blind Controlled Study", Arthritis and Rheumatism 14, 727–732 (1971).
Plewig et al., "Anti-Inflammatory Effects of Antimicrobial Agents: An *In Vivo* Study", Journal of Investigative Dermatology 65, 532–536 (1975).
White, J. E., "Minocycline for Dystrophic Epidermolysis Bullosa", *Lancet*, 966 (1989).
Delaisse et al., "A New Synthetic Inhibitor of Mammalian Tissue Collagenase Inhibits Bone Resorption in Culture", Biochemical and Biophysical Research Communications 133, 483–490 (1985).
Cowen et al., "Monensin Inhibits Collagenase Production in Osteoblastic Cell Cultures and Also Inhibits Both Collagenase Release and Bone Resorption in Mouse Calvaria Cultures", Biochemistry International 11, 273–280 (1985).
Wong et al., "Oral Ibuprofen and Tetracycline for the Treatment of Resistant Acne Vulgaris", Journal of the American Academy of Dermatology 11, 1076–1081 (1984).
Funt, L. S., "Oral Ibuprofen and Minocycline for the Treatment of Acne Vulgaris", Journal of the American Academy of Dermatology, 13, 524–525 (1985).
Golub et al., "In Vivo Crevicular Leukocyte Response to a Chemotactic Challenge: Inhibition by Experimental Diabetes", Infection and Immunity 37, 1013–1020 (1982).
Yu et al., "Serum Levels of Chemically-Modified Tetracycline (CMT): a Composition to Tetracycline (TC)", J. Dent. Res. 69, 245 (Special Issue), IADR Special Abstract No. 1092.

*Primary Examiner*—Shep K. Rose
*Attorney, Agent, or Firm*—Hoffmann & Baron

[57] ABSTRACT

A method for treating mammals suffering from skeletal muscle wasting and/or intracellular protein degradation of skeletal muscle systems by administering to the mammal an amount of tetracycline which results in a significant reduction of the muscle wasting and protein degradation is disclosed. In addition, there is also disclosed a method of increasing the protein content of skeletal muscle systems of mammals by administration of tetracyclines. The tetracyclines useful in the above methods are both antimicrobial and non-antimicrobial. In a preferred embodiment, the method of treatment utilizes a non-antimicrobial tetracycline such as dedimethylaminotetracycline (CMT).

24 Claims, No Drawings

INHIBITION OF WASTING AND PROTEIN DEGRADATION OF MAMMALIAN MUSCLE BY TETRACYCLINES

BACKGROUND OF THE INVENTION

The present invention relates to an anti-proteolytic composition useful in the treatment of protein wasting disorders. In particular, the present invention relates to compositions useful in the treatment of muscle wasting disorders and intracellular protein degradation disorders of mammalian skeletal muscle systems.

Tetracyclines constitute a family of well known natural and synthetic broad spectrum antibiotics. The parent compound, tetracycline, exhibits the following general structure:

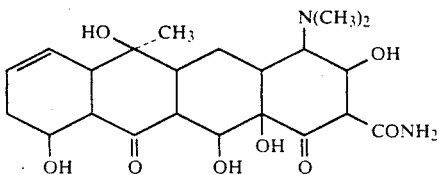

The numbering system of the ring nucleus is as follows:

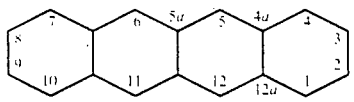

Tetracycline as well as the 5-OH (terramycin) and 7-Cl (Aureomycin) derivatives exist in nature, and are well known antibiotics. Natural tetracyclines may be modified without losing their antibiotic properties, although certain elements of the structure must be retained. The modifications that may and may not be made to the basic tetracyline structure have been reviewed by Mitscher in *The Chemistry of Tetracyclines*, Chapter 6. According to Mitscher, the substituents at positions 5-9 of the tetracycline ring system may be modified without the complete loss of antibiotic properties. Changes in the basic ring system or replacement of the substituents at positions 1-4 and 10-12, however, generally lead to synthetic tetracyclines with substantially less or effectively no antibacterial activity. For example, 4-dedimethylamino-tetracycline is commonly considered to be a non-antibacterial tetracycline.

Various properties of antimicrobial and non-antimicrobial tetracyclines are known. Most commonly known is the bacteriostatic activity of the antimicrobial tetracyclines. Additionally, both antimicrobial and non-antimicrobial tetracyclines are known inhibitors of collagen degrading enzymes such as mammalian collagenase, macrophage elastase and bacterial collagenase; Golub, et al., *J. Periodont. Res.* 20, 12-23 (1985) and Golub, et al., *J. Periodont. Res.* 1990, in press. Collagen is a major component of connective tissue matrices such as those in bone, synovium, eye, skin, tendons and gingiva. Collagenase, which is naturally produced by only a few types of bacteria and in a number of tissues and cells in mammals, degrades collagen.

U.S. Pat. No. 4,704,383 to McNamara, et al. discloses that tetracyclines having substantially no effective antibacterial activity inhibit collagenolytic enzyme activity in rats. McNamara, et al. also report that non-antimicrobial tetracyclines reduce bone resorption in organ culture.

Earlier, U.S. Pat. No. 4,666,897 to Golub, et al. disclosed that tetracyclines in general, including commercially-available antimicrobial forms of the drug, inhibit excessive bone resorption and collagenolytic enzyme activity.

The effects of tetracyclines on rates of degradation of intracellular proteins has not been investigated. In particular, the effects of these agents on rates of degradation of skeletal muscle intracellular proteins has not been reported. Therefore, an effect of tetracyclines has not been established, however, for mammals with skeletal muscle wastinq or disorders of the mammalian skeletal muscle system characterized by intracellular protein degradation.

In humans, there is a variety of disorders in which protein wasting in skeletal muscles and intracellular protein degradation in skeletal muscle play a prominent role. Examples of such diseases include uncontrolled diabetes mellitus, cachexia of cancer, acquired immune deficiency syndrome (AIDS), burns, trauma, etc. Muscle wasting and protein degradation result in muscle weakness, fatigue and loss of function.

Insulin, naturally occurring in mammals, and the mainstay of treatment for hyperglycemia, is known to inhibit protein degradation and stimulate protein synthesis in the skeletal muscle system of mammals. While useful in the treatment of the hyperglycemic disease, diabetes mellitus, the use of insulin in non-hyperglycemic mammals having diseases associated with muscle wasting and/or protein degradation can be lethal, because the potent hypoglycemic action of insulin severely limits its use as an anti-proteolytic in non-hyperglycemic mammals.

Oral hypoglycemics, such as glyburide, have also been shown to have an anti-proteolytic effect similar to that of insulin. Co-inventors herein, Gorray, Maimon and Schneider disclose significant depression of protein degradation by using glyburide on rat $L_6$ myoblasts, *Metabolism* 39, No. 2, 109-116 (1990). Oral hypoglycemics, however, like insulin, are impracticable as anti-proteolytic agents in non-hyperglycemic mammals.

It is therefore an object of the present invention to provide a method useful in the treatment of skeletal muscle wasting and muscle intracellular protein degradation disorders which does not suffer from the drawbacks of the methods disclosed above which rely upon administering hypoglycemic agents.

It is a further object of the present invention to provide a method of promoting protein synthesis in skeletal muscle systems exhibiting excessive proteolytic action.

SUMMARY OF THE INVENTION

In accordance with the present invention, there is provided a method for treating mammals suffering from skeletal muscle wasting and/or excess proteolytic protein degradation in the skeletal muscle system. The method includes administering to the mammal an amount of a tetracycline which results in significant reduction of skeletal muscle wasting and/or protein degradation.

The present invention further includes a method of promoting protein synthesis in the skeletal muscle system of mammals exhibiting muscle wasting. The promotion of protein synthesis is also achieved by administering to the mammal an amount of a tetracycline which results in an increase in the intracellular protein content of the skeletal muscle system.

Tetracyclines useful in the method of the present invention include both antimicrobial and non-antimicrobial tetracyclines. Examples of suitable antimicrobial tetracyclines include commonly available tetracycline hydrochloride, doxycycline and minocycline. In a preferred embodiment, the tetracycline administered is effectively non-antimicrobial. Examples of such preferred tetracyclines include dedimethylaminotetracyclines such as 4-dedimethylaminotetracycline, 4-dedimethylamino-5-oxytetracycline, 6-deoxy-6-demethyl-4-dedimethylaminotetracycline and 7-chloro-6-demethyl-4-de-dimethylaminotetracycline and the 6-α-deoxy-5-hydroxy-4-dedimethylaminotetracycline.

The amount of tetracycline used in the method of the present invention may be generally described as that amount which effectively inhibits skeletal muscle wasting, intracellular protein degradation in skeletal muscle and/or promotes protein synthesis in the skeletal muscle system of mammals. For example, the antimicrobial tetracycline doxycycline, may be administered in amounts ranging from about 0.1 to about 4.0 mg/kg/day. The non-antimicrobial tetracycline, CMT, may be administered in amounts ranging from about 0.1 to about 30 mg/kg/day. Naturally, the dosages of the various tetracycline analogs will vary somewhat from each other and the ranges set forth above are illustrative of only two possible choices. Those skilled in the art will determine optimal dosing of the tetracycline selected from clinical experience in order to carry out the present method of treatment.

As a result of the present invention, mammals suffering from skeletal muscle wasting and/or excessive proteolytic activity in the skeletal muscle system may now be effectively treated to prevent and/or reverse skeletal muscle wasting. Mammals with chronic disease processes such as diabetes mellitus, AIDS, inherited and/or acquired muscular dystrophies, and other diseases which have skeletal muscle wasting as a part of the disease process, may be relieved of at least the muscle wasting part of their malady. The method not only inhibits protein degradation in the skeletal muscle system but also promotes synthesis in the skeletal muscle system. The method, therefore, offers easing of mammalian suffering due to muscle weakness and atrophy.

For a better understanding of the present invention, together with other and further objects, reference is made to the following detailed description, and its scope will be pointed out in the appended claims.

DETAILED DESCRIPTION OF THE INVENTION

In accordance with the present invention, a method for treating mammals suffering from skeletal muscle wasting and/or excessive proteolytic degradation in the skeletal muscle system is disclosed. The method comprises administering to the mammal an amount of a tetracycline that results in a significant reduction of mammalian muscle wasting and/or protein degradation.

The tetracyclines useful in carrying out the method of the present invention may be selected from both antimicrobial and non-antimicrobial tetracyclines. In the instance where an antimicrobial tetracycline is selected, such tetracyclines include those well known in the art such as tetracycline hydrochloride, minocycline, doxycycline, chlortetracycline, oxytetracycline and demeclocycline. In a preferred embodiment, the tetracycline is modified so as to reduce its antimicrobial properties. Methods for reducing the antimicrobial properties of a tetracycline are disclosed in *The Chemistry of the Tetracyclines*, Chapter 6, Mitscher, Ed., at page 211. As pointed out by Mitscher, modification at positions 1, 2, 3, 4, 10 and 12a lead to loss of antimicrobial activity. Such modified tetracyclines are included in the preferred embodiment of the present invention, since they can be used without disturbing the normal flora of the treated mammal as would happen with extended exposure to antimicrobial tetracyclines.

Examples of such preferable tetracyclines include those lacking dimethylamino side chain at position 4. Such chemically modified tetracyclines (or CMT's) include, for example, 4-dedimethylaminotetracycline, 4-dedimethylamino-5-oxytetracycline, 4-dedimethylamino-7-chlorotetracycline, 4-hydroxy-4-dedimethylaminotetracycline, 6-demethyl-6-deoxy-4-dedimethylaminotetracycline, and 6-o-deoxy-5-hydroxy-4-dedimethylaminotetracycline.

Further examples of tetracyclines modified for reduced antimicrobial activity include 6-α-obenzylthiomethylenetetracycline, the mono-N-alkylated amide of tetracycline, 6-fluoro-6-demethyltetracycline, or 11α-chlorotetracycline.

The amount of tetracycline administered to inhibit mammalian muscle wasting and intracellular skeletal muscle protein degradation is an amount that significantly reduces muscle wasting and intracellular skeletal muscle protein degradation activity. The maximal dosage for humans is the highest dosage that does not cause clinically important side effects. For the purpose of the present invention, side effects include clinically important disruption of the normal flora as well as toxic effects.

For illustrative purposes, a suitable amount of the antimicrobial tetracycline, doxycycline, is 0.1-4.0 mg/kg/day. In the case of a non-antimicrobial tetracycline, for example, the dose for 4-dedimethylaminotetracycline can be 0.1 to 30 mg/kg/day. However, in either case, the preferred method of treatment includes tetracycline compositions administered in suitable pharmaceutical carriers. The pharmaceutical carrier may be in the form of a capsule, compressed tablet, solution or suspension suitable for oral administration of the tetracycline to the effected mammal. In addition, other means of administration are contemplated, such as by injection either intramuscularly or intravenously.

In an alternative embodiment, there is provided a method of promoting synthesis in these skeletal muscle systems of mammals which includes administering to the mammal an amount of a tetracycline which results in an increase in the protein content of the skeletal muscle system. Similar to the method of treating skeletal muscle wasting, the method for promoting protein synthesis includes tetracyclines which are both antimicrobial such as tetracycline hydrochloride, minocycline, doxycycline, oxytetracycline, chlortetracycline and demeclocycline, as well as non-antimicrobial tetracyclines such as dedimethylaminotetracyclines (CMT's) and related compounds. The present invention's promotion of protein synthesis in skeletal muscle systems is achieved by administering a tetracycline in an amount of from about 0.1 mg/kg/day to 30 mg/kg/day.

Tests were conducted using the method of the present invention's inhibition of skeletal degradation and comparing it to both untreated disease progression and other known anti-proteolytic compounds to observe the anti-proteolytic activity.

EXAMPLES

The following Examples serve to provide further appreciation of the invention but are not meant in any way to restrict the effective scope of the invention.

EXAMPLES I-III

In these Examples, the inhibition of protein degradation by dedimethylaminotetracycline (CMT), minocycline and doxycycline was evaluated and compared against a Control having no protein degradation inhibitor and other Controls having various concentrations of insulin, a known inhibitor of protein degradation and stimulator of protein synthesis in the skeletal muscle systems of mammals. Intracellular proteins within rat $L_6$ myoblasts were biosynthetically labelled in cell culture by exposure to $C^{14}$-tyrosine in a manner similar to that disclosed in *Metabolism* 39, No. 2, 109–116 (1990), by co-inventors herein, Gorray, Maimon, and Schneider. The amino acid tyrosine is neither synthesized nor degraded by skeletal muscle cells, thus, radioactively-labelled tyrosine provides a useful marker for both protein synthesis and degradation.

When the myoblast cells had grown to confluence, the media was replaced with a solution containing Ham's media with 1% bovine serum albumin without fetal calf serum. The absence of fetal calf serum acts to starve the cells providing a model conducive for evaluating protein degradation because the basal rate is increased.

Solutions containing various tetracycline analogs and Controls were added to separate vials containing the cultured myoblasts and incubated for 20 hours at 37° C. in 5% carbon dioxide in air. After incubation, the cells were microfuged and the rate of protein degradation was assessed by measuring the amount of radioactive tyrosine in the supernatant and expressed as a percent radioactivity released over total radioactivity. The concentrations of the tetracycline analogs and Controls in the individual myoblast cell systems are set forth below in Table I.

TABLE I

|  | Controls | | | | Example I | Example II | Example III |
| --- | --- | --- | --- | --- | --- | --- | --- |
|  | A | B | C | D |  |  |  |
| Protein Degradation Inhibitor | None | Insulin | | | CMT | Minocycline | Doxycycline |
| conc. (μg/ml) | — | 0.1 | 1.0 | 10 | 64 | 30 | 30 |
| % Release of Tyrosine | 45.1 | 34.7 | 29.4 | 27.7 | 23.0 | 37.5 | 33.8 |
| Reduction in degradation v. control myoblast activity (A) (percent) | — | 23 | 35 | 39 | 49 | 17 | 25 |

Referring now to Table I, it can be seen that both antimicrobial (minocycline and doxycycline) and non-antimicrobial (CMT) tetracyclines are significant inhibitors of skeletal muscle cell protein degradation. It is also observable that the activities of the various tetracycline analogs compare quite favorably to the inhibition of protein degradation provided by insulin. These tetracyclines have been shown not to reduce the severity of hyperglycemia in the diabetic rat, see Example XXIII and Table IV. While not shown in Table I, the inhibition of protein degradation by tetracycline analogs was demonstrable at concentrations as low as 1 μg/ml. Moreover, the effects of such inhibition were observable within two hours of exposure to the various tetracycline analogs and persisted for the entire duration of the evaluation period, 36 hours.

EXAMPLES IV-XII

In these Examples, the protein degradation inhibiting properties of the tetracycline analogs were evaluated in combination with insulin using the cultured myoblast system described in Examples I-III. The protein degradation inhibition of the tetracycline-insulin combination was compared to that of insulin alone in inhibiting protein degradation. The concentrations of the tetracyclines and insulin and rate of protein degradation, expressed as percent release, are set forth below in Table II. For the purposes of illustration, the Control data illustrated in Table I are repeated in Table II for the purposes of comparison.

TABLE II (Part 1)

|  | Controls | | | | Example IV | Example V | Example VI |
| --- | --- | --- | --- | --- | --- | --- | --- |
|  | A | B | C | D |  |  |  |
| Protein Degradation Inhibitor | None | Insulin | | | CMT 64.0 Insulin 0.1 | CMT 64.0 Insulin 1.0 | CMT 64.0 Insulin 10.0 |
| conc. (μg/ml) | — | 0.1 | 1.0 | 10 |  |  |  |
| % Release of Tyrosine | 45.1 | 34.7 | 29.4 | 27.7 | 15.2 | 13.0 | 13.5 |
| Reduction in degradation v. control myoblast activity (A) (percent) | — | 23 | 35 | 39 | 66 | 71 | 70 |

(Part 2)

TABLE II-continued

| | Example VII | Example VIII | Example IX | Example X | Example XI | Example XII |
|---|---|---|---|---|---|---|
| Protein Degradation Inhibitor conc. (μg/ml) | Minocycline 30 Insulin 0.1 | Minocycline 30 Insulin 1.0 | Minocycline 30 Insulin 10.0 | Doxycycline 30 Insulin 0.1 | Doxycycline 30 Insulin 1.0 | Doxycycline 30 Insulin 10.0 |
| % Release of Tyrosine | 26.8 | 19.0 | 17.4 | 25.0 | 18.0 | 16.1 |
| Reduction in degradation v. control myoblast activity (A) (percent) | 41 | 58 | 61 | 45 | 60 | 64 |

Referring now to Table II, it can be seen that both antimicrobial and non-antimicrobial tetracyclines dramatically augment the effect of insulin on the inhibition of skeletal muscle degradation. For example, insulin alone, at a concentration of 0.1 μg/ml, Control B, reduces tyrosine release by 23% when compared to control muscle degradation. The further addition of CMT 64 μg/ml, however, as shown in Example IV, results in a 66% reduction of tyrosine released by the myoblast.

Similarly, Example V demonstrates a 71% reduction in tyrosine release, while Examples VI–XII demonstrate at least a 41% decrease in tyrosine released by the myoblasts. Furthermore, each of the combined tetracycline-insulin Examples exceeded the inhibiting properties of insulin alone, even when insulin was present in maximally effective doses.

The therapeutic benefits of administering tetracyclines according to the method of the present invention for combatting muscle wasting disorders may thus be realized either as a separate treatment or in combination with added exogenous insulin for reducing skeletal muscle wasting. Further, the results as shown in Table II demonstrate that tetracycline analogs have a mechanism of action separate from that of insulin and allow inhibition of skeletal muscle protein degradation independent from that of insulin. There is an additive effect when a tetracycline analog is added to maximally effective concentrations of insulin.

EXAMPLES XIII–XXII

In these Examples, the inhibition of protein degradation using the method of the present invention, both with and without added insulin was observed at different time intervals using the cultured rat myoblasts similar to that of the previous Examples. In particular, the amount of skeletal muscle protein degradation was observed by measuring the radioactively-labelled tyrosine released at differing time intervals. The protein degradation was expressed as a percentage of $C^{14}$-tyrosine released from pre-labeled myoblasts. The tetracycline analogs CMT, minocycline (MIN) and doxycycline (DOX) were compared alone and combined with insulin against a Control having no inhibitor and an insulin only Control. In these Examples, all data reflect the mean of four separate measurements of the myoblasts at the time interval. All concentrations are expressed in μg/ml. The results are set forth in Table III below.

TABLE III

The Effect of Various Treatments on Protein Degradation In Myoblasts In Cell Culture At Three Different Incubation Times

| | | Time Interval | | |
|---|---|---|---|---|
| EXAMPLE | Inhibitor (conc.) | 4.5 hr. | 20 hr. | 28 hr. |
| Control | No Inhibitor | 5.0 | 28.8 | 33.1 |
| Control | Insulin 5 | 3.5 | 18.7 | 22.0 |
| XIII | CMT 16 | 4.8 | 26.9 | 31.0 |
| XIV | CMT 32 | 5.0 | 24.9 | 27.6 |
| XV | CMT 64 | 4.7 | 20.9 | 23.6 |
| XVI | Min 30 | 4.9 | 24.4 | 28.2 |
| XVII | Dox 30 | 4.8 | 21.5 | 25.4 |
| XVIII | Insulin 5 + CMT 16 | 3.6 | 16.6 | 18.7 |
| XIX | Insulin 5 + CMT 32 | 3.8 | 13.9 | 15.6 |
| XX | Insulin 5 + CMT 64 | 3.5 | 13.4 | 14.8 |
| XXI | Insulin 5 + Min 30 | 3.6 | 14.0 | 15.6 |
| XXII | Insulin 5 + Dox 30 | 3.7 | 12.8 | 15.0 |

All concentrations in μg/ml

Referring now to Table III, it can be seen that protein degradation increases in skeletal muscle systems with time between 4.5 hours and 28 hours. Like insulin, tetracycline analogs alone have the ability to inhibit protein degradation. Further, there is a demonstrable dose-related effect on inhibition of protein degradation by CMT between concentrations of 16–64 μg/ml. Finally, the results demonstrated in Table III suggest that when tetracycline analogs are combined with insulin, a synergistic effect for inhibiting protein degradation is obtained. The inhibition shown by combinations of tetracyclines and insulin are profoundly greater than is observable with either insulin or tetracycline alone. These Examples comport with the results shown in Examples IV–XII.

EXAMPLE XXIII

In this Example, an in vivo study was undertaken to observe the ability of CMT to inhibit muscle wasting and atrophy often associated with chronic disease processes. Using a group of adult Sprague-Dawley rats, four rats were preserved as Controls, while eight rats were made insulin-deficient by injection of the diabetogenic agent, streptozotocin according to the method set forth, for example, by Golub, et al., in *Infect. Immun.* 37: 1013 (1982). The diabetic rats were divided into two equal groups of four with the first group receiving 10 mg. of 4-dedimethylaminotetracycline (CMT) daily, and the other group was untreated. On the twenty-first day after initiation of CMT treatment, all of the rats in each of the groups were sacrificed by exsanguination under Halothane anesthesia. The blood was collected intra-cardially and analysis for CMT was undertaken using a high pressure liquid chromatography (HPLC) technique as described by Yu, et al., *J. Dent. Res.* 69: 245

(Special Issue), IADR Abstr. No. 1092. The blood samples were also anlayzed for glucose concentration using standard spectrophotometric techniques. The results are set forth for each group in Table IV below. Note, each value represents the mean of four animals per group +/− standard error of the mean.

In addition, the gastrocnemius muscles were disected from both of the hind limbs of each rat to determine the amount of wasting and atrophy of the muscle. The average results for each group for this analysis are also set forth in Table IV below.

TABLE IV

| Experimental Group | Serum Concentration | | Skeletal Muscle | | |
|---|---|---|---|---|---|
| | glucose (mg/dL) | CMT (µg/mL) | wet weight (g) | diameter (cm) | length (cm) |
| Non-Diabetic Controls | 107 ± 13 | 0 ± 0 | 2.73 ± 0.04 | 18.0 ± 0.6 | 31 ± 0.5 |
| Diabetics | 743 ± 133 | 0 ± 0 | 1.59 ± 0.18 | 13.3 ± 0.2 | 27 ± 0.6 |
| Diabetics + CMT | 776 ± 19 | 6.8 ± 0.9 | 2.31 ± 0.09 | 17.7 ± 0.4 | 28 ± 0.6 |

Referring now to TABLE IV, it can be seen that CMT demonstrates significant inhibition of muscle wasting in vivo; also note that the CMT prevented muscle wasting without reducing the severity of hyperglycemia in the diabetics. For example, the untreated diabetic rats lost an average of 42% of their skeletal muscle wet weight, while those rats treated with CMT lost only 15% of their wet weight. Similarly, Table IV shows that by treating diabetic rats with CMT, muscle diameter can be essentially retained at control levels. Untreated diabetic rats, on the other hand, suffered a 26% decrease in muscle diameter.

As can be seen from the above Examples, the present invention provides a significant improvement in the treatment of skeletal muscle wasting associated with intracellular protein degradation. It has been demonstrated that both antimicrobial and non-antimicrobial tetracyclines are effective in the method of treatment according to the present invention. Further, the method of the present invention's inhibition of skeletal muscle wasting and promotion of increased muscle mass in the skeletal muscle area provide useful adjuncts to the treatment of muscle wasting disorders in mammals with chronic diseases such as diabetes and/or muscular dystrophies.

While there have been described what are presently believed to be the preferred embodiments of the present invention, those skilled in the art will realize that changes and modifications may be made thereto without departing from the spirit of the invention, and it is intended to claim all such changes and modifications as fall within the true scope of the invention.

What is claimed is:

1. A method for treating mammals suffering from skeletal muscle wasting comprising:
    administering to said mammal an effective amount of a tetracycline thereby causing a reduction in mammalian skeletal muscle wasting.

2. The method of claim 1, wherein said tetracycline is selected from the group consisting of antimicrobial and non-antimicrobial tetracyclines.

3. The method according to claim 2, wherein said anti-microbial tetracycline is selected from the group consisting of tetracycline hydrochloride, ninocycline, doxycycline, oxytetracyclihne, chlortetracycline and demeclotetracycline.

4. The method according to claim 2, wherein said non-antimicrobial tetracycline is a dedimethylaminotetracycline.

5. The method according to claim 4, wherein said dedimethylaminotetracycline is selected from the group consisting of 4-de(dimethylamino)-tetracycline, 4-de(-dimethylamino-5-oxytetracycline,. 4-de(dimethylamino)-7-chlorotetracycline, 4-hydroxy-4-dedimethylaminotetracycline, 6-demethyl-6-deoxy-4-dedimethylaminotetracycline, and 6-α-deoxy-5-hydroxy-4-dedimethylamino-tetracycline.

6. The method according to claim 1, wherein said tetracycline is selected from the group consisting of 6α-benzylthiomethylenetetracycline, the mono-N-alkylated amide of tetracycline, 6-fluoro-6-demethyltetracycline, and 11α-chlorotetracycline.

7. The method according to claim 1, wherein said tetracycline is administered in an amount of from about 0.1 mg/kg per day to about 30 mg/kg per day.

8. The method according to claim 1, wherein said tetracycline is administered in an amount of from about 0.2 mg/kg per day to about 15 mg/kg per day.

9. A method of promoting protein synthesis in skeletal muscle systems of mammals comprising:
    administering to said mammal an effective amount of a tetracycline thereby causing an increase in protein content of said skeletal muscle system.

10. The method of claim 9, wherein said tetracycline is selected from the group consisting of antimicrobial and non-antimicrobial tetracyclines.

11. The method according to claim 10, wherein said anti-microbial tetracycline is selected from the group consisting of tetracycline hydrochloride, minocycline, doxycycline, demeclocycline and 7-chloro-tetracycline.

12. The method according to claim 10, wherein said non-antimicrobial tetracycline is a dedimethylaminotetracycline.

13. The method according to claim 12, wherein said dedimethylaminotetracycline is selected from the group consisting of 4-de(dimethylamino) tetracycline, 4-de(-dimethylamino)-5-oxytetracycline, 4-de(dimethylamino)-7chlorotetracycline, 6-α-deoxy-5-hydroxy-4-dedimethylamino-tetracycline, 7-chloro-6-demethyl-4-dedimethylamino-tetracycline, and 4-hydroxy-4dedimethylaminotetracycline.

14. The method according to claim 9, wherein said tetracycline is selected from the group consisting of 6α-benzylthiomethylenetetracycline, the mono-N-alkylated amide of tetracycline, 6-fluoro-6-demethyltetracycline, and 11α-chlorotetracycline.

15. The method according to claim 9, wherein said tetracycline is administered in an amount of from about 0.1 mg/kg per day to about 30 mg/kg per day.

16. The method according to claim 9, wherein said tetracycline is administered in an amount of from about 0.2 mg/kg per day to about 15 mg/kg per day.

17. A method for treating mammals suffering from excess proteolytic degradation in the skeletal muscle system of said mammal comprising:

administering to said mammal an amount of a tetracycline that results in significant reduction of excess proteolytic degradation in the skeletal muscle 18. The method of claim 17, wherein said tetracycline is selected from the group consisting of antimicrobial and non-antimicrobial tetracyclines.

19. The method according to claim 18, wherein said anti-microbial tetracycline is selected from the group consisting of tetracycline hydrochloride, minocycline, doxycycline, demeclocycline and 7-chlorotetracycline.

20. The method according to claim 17, wherein said non-antimicrobial tetracycline is a dedimethylaminotetracycline.

21. The method according to claim 20, wherein said dedimethylaminotetracycline is selected from the group consisting of 4-de(dimethylamino)-tetracycline, 4-de(-dimethylamino)-5-oxytetracycline, 4-de(dimethylamino)-7-chlorotetracycline, 4-hydroxy-4-dedimethylaminotetracycline, 6-demethyl-6-deoxy-4-dedimethylaminotetracycline and 6-α-deoxy-5-hydroxy-4-dedimethylamino-tetracycline.

22. The method according to claim 17, wherein said tetracycline is selected from the group consisting of 6α-benzylthiomethylenetetracycline, the mono-N-alkylated amide of tetracycline, 6-fluoro-6-demethyltetracycline, and 11α-chlorotetracycline.

23. The method according to claim 17, wherein said tetracycline is administered in an amount of from about 0.1 mg/kg per day to about 30 mg/kg per day.

24. The method according to claim 17, wherein said tetracycline is administered in an amount of from about 0.2 mg/kg per day to about 15 mg/kg per day.

* * * * *